United States Patent
Morazzoni et al.

(10) Patent No.: US 8,772,251 B2
(45) Date of Patent: Jul. 8, 2014

(54) USE OF ISOTHIOCYANATE DERIVATIVES AS ANTI-MYELOMA AGENTS

(75) Inventors: Paolo Morazzoni, Milan (IT); Carla Manzotti, Milan (IT); Gabriele Fontana, Milan (IT); Antonella Riva, Milan (IT); Renato Iori, Milan (IT)

(73) Assignee: Indena S.p.A., Milan (IT)

( * ) Notice: Subject to any disclaimer, the term of this patent is extended or adjusted under 35 U.S.C. 154(b) by 722 days.

(21) Appl. No.: 12/812,970

(22) PCT Filed: Dec. 17, 2008

(86) PCT No.: PCT/EP2008/010768
§ 371 (c)(1),
(2), (4) Date: Sep. 9, 2010

(87) PCT Pub. No.: WO2009/089889
PCT Pub. Date: Jul. 23, 2009

(65) Prior Publication Data
US 2011/0053870 A1    Mar. 3, 2011

(30) Foreign Application Priority Data
Jan. 18, 2008    (EP) ................................ 08100658

(51) Int. Cl.
*A61K 31/7034*    (2006.01)
(52) U.S. Cl.
USPC ......................................................... 514/25
(58) Field of Classification Search
USPC ......................................................... 514/25
See application file for complete search history.

(56) References Cited

U.S. PATENT DOCUMENTS

2002/0151505 A1    10/2002    Fahey

FOREIGN PATENT DOCUMENTS

WO    2006/065736    6/2006

OTHER PUBLICATIONS

Kyle et al., British Journal of Haematology, 2003, 121, 749-757.*
Definition of plasmacytoma, Dorland's Illustrated Medical Dictionary, http://www.credoreference.com/entry/ehsdorland/plasmacytoma, accessed online on Sep. 13, 2012.*
Barillari et al., J. Agric. Food Chem., 2005, 53, p. 2475-2482.*
Parvathy et al., Trends in Medical Research, 2007, 2(1), p. 44-50.*
Zhang et al., Mol. Cancer Ther., 2003, 2, p. 1045-1052.*
Guevara A. et al., "An Antitumor Promoter from Moringa Oleifera Lam" Mutation Research, vol. 440, No. 2, 1999, pp. 181-188.
Leoni, O. et al., "Myrosinase-Generated Isothiocyanate from Glucosinolates: Isolates, Characterization and In Vitro Antiproliferative Studies" Bioorganic & Medical Chemistry, vol. 5, No. 9, 1997, pp. 1799-1806.
Bennet R., et al., "Profiling Glucosinolates and Phenolics in Vegetative and Reproductive Tissues of the Multi-purpose Trees Moringa Oleifera L. and Moringa Stenopetala L" Journal of Agricultural and Food Chemistry, vol. 51, No. 12, Apr. 4, 2003, pp. 3546-3553.
Trees for Life Journal, vol. 1, No. 5, Dec. 1, 2005.

* cited by examiner

Primary Examiner — Shaojia Anna Jiang
Assistant Examiner — Jonathan S Lau
(74) Attorney, Agent, or Firm — Silvia Salvadori, P.C.

(57) ABSTRACT

The invention concerns the use of glucomoringin and of its des-thio-glucoside having the following formulae (I, II): for the preparation of a medicament for the treatment of myeloma.

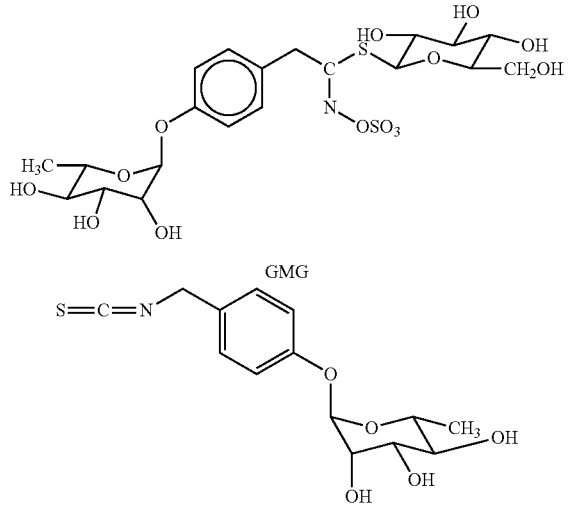

4 Claims, No Drawings

USE OF ISOTHIOCYANATE DERIVATIVES AS ANTI-MYELOMA AGENTS

This application is a U.S. national stage of PCT/EP2008/010768 filed on Dec. 17, 2008 which claims priority to and the benefit of European Application No. 08100658.7 filed on Jan. 18, 2008, the contents of which are incorporated herein by reference.

The present invention refers to the use of glucomoringin or of the corresponding isothiocyanate derivative as anti-myeloma agents.

BACKGROUND OF THE INVENTION

Vegetables are the most important source of compounds with chemopreventive activity: among them, the isothiocyanates (ITCs) produced in Brassicaceae (e.g. broccoli, Brussels sprouts, cauliflower, etc.) have currently drawn a lot of interest since Sidransky's first study about ITC-induced tumor growth inhibition [1].

In vegetables, ITCs are stored in the form of inactive precursors called glucosinolates (GLs) and can be released after tissue damage by enzymatic hydrolysis involving myrosinase (MYR, E.C. 1.2.1.147), a thioglucoside glucohydrolase that is physically separated from GLs under normal conditions [2,3].

As the intestinal microflora of mammals, including humans, has myrosinase-like activity, GLs can also be converted into ITCs in their digestive tract [4,5].

ITCs have been reported to be inhibitors of tumor growth in different in vivo preclinical studies [6-8] and moreover epidemiological studies have shown an inverse relationship between dietary consumption of Brassicaceae and risk of developing lung, breast and colon cancer [9-11].

ITCs have many effects through which they exhibit their protective action against cancer progression: they can i) induce phase-2-enzymes like glutathione-S-transferase (GST) and quinone-reductase (QR) [12-15] through a Nrf-2 pathway, ii) cause cell cycle arrest and apoptosis [16-18], iii) inhibit phase-I-enzymes and NF-kB related genes [19,20].

Sulforaphane has been extensively studied in recent years, due to its role as a chemopreventive agent and various studies have demonstrated its potential use as a novel chemotherapeutic compound [7, 11, 20].

Glucomoringin (GMG) is an uncommon member of the glucosinolates (GLs) family and presents a unique characteristic consisting in a second saccharidic residue in its side chain. This GLs is a typical secondary metabolite present in vegetables belonging to the genus Moringaceae that consists of 14 species, among which *M. oleifera* is the most widely distributed. *M. oleifera* is a multipurpose tree which grows in many tropical or equatorial regions. The medical value of the seeds and other part of the plant have long been recognized in folk medicine [21]. The glycosylated isothiocyanates (GMG-ITC), resulting from myrosinase-hydrolysis of GMG, has been shown to exhibit a broad biological activity and it was also shown to exert an effective antitumor promoting activity [22]. GMG-ITC can be purified in high amount starting from pure GMG. GMG-ITC is a solid, odourless and stable compound at room temperature differing from others natural bioactive ITCs which are liquid, volatile, with pungent odour.

Multiple myeloma is a malignant disease of plasma cells that is characterized by skeletal destruction, renal failure, anemia and hypercalcemia [23]. The median age at diagnosis is 68 years. Myeloma accounts for 1% of all malignant disease in white population and 2% in black population and 13% and 33% respectively, of all hematological cancers [24].

Treatments for myeloma include supportive treatment and infusional chemotherapy followed for younger patients by high dose chemotherapy and an autologous transplant [25]. Exploitation of the understanding of the biology of myelomas lead to development of new therapeutic approaches[26]. Although major progress has been made in treating myeloma with this new therapies, there is no role at present for the replacement of the standard cure. Thus, there is a continuing need for new, more active and/or alternative agents.

DESCRIPTION OF THE INVENTION

It has now been found that glucomoringin (GMG) or its des-thio-glucoside (GMG-ITC) having the following formulae:

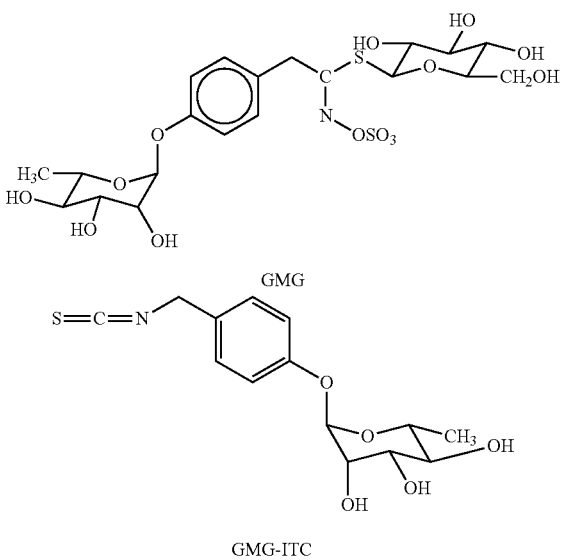

are endowed with a remarkable cytotoxic activity against myeloma cell lines. The activity has also been confirmed in vivo in experimental models.

The invention accordingly concerns the use of either GMG or GMG-ITC for the preparation of a medicament for the treatment of myelomas, particularly for the treatment of multiple myeloma.

For the considered therapeutic use, GMG or GMG-ITC will be suitably formulated in dosage forms, particularly for enteral or parenteral administration, according to well known methods.

Examples of suitable compositions include tablets, capsules, sterile solutions or suspensions for intramuscular or intravenous injection, and the like. The actual doses and therapeutic protocols will depend as usual on several factors, namely pharmacokinetic and toxicological characteristics, patient's conditions (weight, sex and age), stadiation of the disease. A skilled practitioner will easily determine the most effective dosage regimen according to the established methods. It is believed that the effective therapeutic doses in humans will range between 1 mg/Kg/day to 30 mg/Kg/day, even though higher dosages cannot be ruled out also in view of the limited toxicity of both GMG and GMG-ITC.

GMG and GMG-ITC may be used as a single therapy or in combination with other known chemotherapeutic agents already available for the treatment of myeloma.

The invention will now be described in more detail in the following examples.

Example 1

Isolation and Purification of Compounds

GMG and GRA were isolated respectively from *Moringa oleifera* L. (fam. Moringaceae) and *Brassica oleracea* L. (fam. Brassicaceae; var. *acephala*; subvar. *laciniata*) seeds. Both GLs were purified in two sequential steps, by anion exchange and size exclusion chromatography, according to previously reported methods [27, 28]. Individual GLs were characterized by $^1H$ and $^{13}C$ NMR spectrometry and the purity was assayed by HPLC analysis of the desulfo-derivative according to the ISO 9167-1 method [29] yielding about 99% based on peak area value, but about 90-92% on weight basis due to their high hygroscopic properties. The enzyme MYR was isolated from seeds of *Sinapis alba* L. according to a reported method [30] with some modifications. The stock solution used in the present study had a specific activity of ~60 units/mg of soluble protein and was kept at 4° C. after dilution in $H_2O$ at 34 U/ml. One MYR unit was defined as the amount of enzyme able to hydrolyze 1 µmole/min of sinigrin at pH 6.5 and 37° C. The MYR solution was stored at 4° C. in sterile distilled water until use. GMG-ITC was produced via myrosinase catalyzed hydrolysis of GMG, performed in 0.1 M phosphate buffer pH 6.5 at 37° C. The reaction mixture was prepared dissolving 7.0 grams of pure GMG in 350 mL of buffer and after 40 U of myrosinase were added the solution were kept at 37° C. for 4-6 hours. The total conversion of pure GMG into GMG-ITC was confirmed by HPLC analysis of the desulfo-derivative [29], which allowed us to monitor the reduction until complete disappearance of GMG in the reaction mixture. Acetonitrile was then added to the mixture until the final concentration was 10% and GMG-ITC was purified by reverse-phase chromatography, which was performed using a HR 16/10 column packed with LiChrospher RP-C18 (MERCK) or SOURCE 15 RPC (Amersham Biosciences), connected to a AKTA-FPLC equipped with Frac-900 fraction collector and UV monitor UPC-900 (Amersham Biosciences). After washing with acetonitrile 10%, elution was carried out with a gradient up to 60% acetonitrile. Fractions were collected and analysed using a Hewlett-Packard Model 1100 HPLC system with an Inertsil ODS3 column (250×3 mm, 5 mm). Chromatography was performed with 1 mL/min flow rate at 30° C. by eluting with a linear gradient of water (A) and acetonitrile (B) from 30% B to 80% in 20 min. Elution of GMG-ITC was detected by a diode array, monitoring the absorbance at 229 nm. Fractions containing GMG-ITC (peak purity>99%) were collected, the solvent were removed by concentration in a rotary evaporator, and the final solution was freeze-dried. The GMG-ITC was characterized and unambiguously identified by $^1H$- and $^{13}C$-NMR and mass spectrometry techniques.

Example 2

Biological Results

In Vitro Data:
Table 1 shows the sensitivity of H460 human lung tumor cell line to glucomoringine. The increase of concentration of GMG in the presence of myrosinase results in a cytotoxic effect.

| | % of cells growth relative to control | | | |
|---|---|---|---|---|
| | 0 | 24 h treatment | 24 h recovery | 48 h recovery |
| Controls | 100 | 100 | 100 | 100 |
| GMG (100 µM) | 100 | 98 | 100 | 100 |
| GMG (7.5 µM) + MYR (0.19 U) | 100 | 75 | 72 | 80 |
| GMG (10 µM) + MYR (0.19 U) | 100 | 63 | 51 | 69 |
| GMG (15 µM) + MYR (0.19 U) | 100 | 33 | 20 | 24 |
| GMG (20 µM) + MYR (0.19 U) | 100 | 28 | 17 | 8 |

Cytotoxic activity of the *Moringa* derived isothiocyanate (GMG-ITC) on a panel of human tumor cell lines. In the same table the values obtained with the ITC sulphorafane (GRA) as a reference standard are reported in the following Table 2.

| | Cell count (24 h) (IC50 (µM)) | |
|---|---|---|
| Cell lines | GMG-ITC | GRA |
| H460 wt | 29 ± 0.8 | 29 ± 0.5 |
| H460 S5 | 18 ± 6.7 | 19 ± 1 |
| MCF7 π | 21 ± 5.7 | 27 ± 4 |
| MCF7 NEO | 20 ± 4.4 | 26 ± 4 |
| HL60 | 15 ± 1 | 16 ± 1 |
| HCT116 p53$^{+/+}$ | 12 ± 0.3 | 17 ± 2.3 |
| HCT116 p53$^{-/-}$ | 13 ± 0.25 | 18 ± 5.3 |
| A2780 | 15 ± 3 | 18 ± 1 |
| RPMI-8226 | 6 ± 1 | 8 ± 0.2 |

The data reported in the Table clearly show that the ITC are more cytotoxic in myeloma cell lines compared to the other tumor cell lines of different tumor type.

In Vivo Studies
In the table 3 is reported the antitumor activity of the GMG-ITC administered in vivo in SCID mice bearing human myeloma tumor cell lines s.c. transplanted.

| Compound | Treatment schedule | Dose (mg/kg/inj.) | TWI % |
|---|---|---|---|
| GMG | p.o. q5dx2 | 400 | 62 |
| GMG-ITC | i.p. q5dx2w | 20 | 70 |

When GMG-ITC was tested in the human ovarian carcinoma A2780 the antitumor activity was low, as reported in the table 4 below.

| Compound | Treatment schedule | Dose (mg/kg/inj.) | TWI % |
|---|---|---|---|
| GMG-ITC | i.p. q5dx2w | 20 | 46 |

REFERENCES

1 Sidransky H, Ito N, Verney E. (1966) Influence of alpha-naphthyl-isothiocyanate on liver tumorigenesis in rats ingesting ethionine and N-2-fluorenylacetamide. *J Natl Cancer Inst.* 1966 November; 37(5):677-86.
2 Fenwick, G. R., Heaney, R. K. & Mullin, W. J. (1983) Glucosinolates and their breakdown products in food and food plants. *CRC Crit. Rev. Food Sci. Nutr.* 18: 123-201

3 Fahey, J. W., Zalcmann, A. T. & Talalay, P. (2001) The chemical diversity and distribution of glucosinolates and isothiocyanates among plants. *Phytochemistry* 56: 5-51.
4 Shapiro T A, Fahey J W, Wade K L, Stephenson K K, Talalay P. (1998) Human metabolism and excretion of cancer chemoprotective glucosinolates and isothiocyanates of cruciferous vegetables. *Cancer Epidemiol Biomarkers Prev.* 1998 December; 7(12):1091-100
5 Getahun S M, Chung F L. (1999) Conversion of glucosinolates to isothiocyanates in humans after ingestion of cooked watercress. *Cancer Epidemiol Biomarkers Prev.* 1999 May; 8(5):447-51
6 Zhang Y, Talalay P. (1994) Anticarcinogenic activities of organic isothiocyanates: chemistry and mechanisms. *Cancer Res.* 1994 Apr. 1; 54(7 Suppl):1976s-1981s. Review.
7 Hecht S S. (2000) Inhibition of carcinogenesis by isothiocyanates. *Drug Metab Rev.* 2000 August-November; 32(3-4):395-411. Review.
8 Conaway, C. C., Yang, Y.-M. & Chung, F.-L. (2002) Isothiocyanates as cancer chemopreventive agents: their biological activities and metabolism in rodents and humans. *Curr. Drug Metab.* 3:233-255.
9 Fowke J H, Chung F L, Jin F, Qi D, Cai Q, Conaway C, Cheng J R, Shu X O, Gao Y T, Zheng W. (2003) Urinary isothiocyanate levels, *brassica*, and human breast cancer. *Cancer Res.* 2003 Jul. 15; 63(14):3980-6.
10 Zhao B, Seow A, Lee E J, Poh W T, Teh M, Eng P, Wang Y T, Tan W C, Yu M C, Lee H P. (2001) Dietary isothiocyanates, glutathione S-transferase-M1, -T1 polymorphisms and lung cancer risk among Chinese women in Singapore. *Cancer Epidemiol Biomarkers Prev.* 2001 October; 10(10):1063-7
11 Conaway C C, Wang C X, Pittman B, Yang Y M, Schwartz J E, Tian D, McIntee E J, Hecht S S, Chung F L. (2005) Phenethyl isothiocyanate and sulforaphane and their N-acetylcysteine conjugates inhibit malignant progression of lung adenomas induced by tobacco carcinogens in A/J mice. *Cancer Res*. September 15; 65(18):8548-57.
12 Steinkellner, H., Rabot, S., Freywald, C., Nobis, E., Scharf, G., Chabicovsky, M., Knasmüller, S. & Kassie, F. (2001) Effects of cruciferous vegetables and their constituents on drug metabolising enzymes involved in the bioactivation of DNA-reactive dietary carcinogens. *Mutat. Res.* 480-481: 285-297.
13 Talalay, P. & Fahey, J. W. (2001) Phytochemicals from cruciferous plants protect against cancer by modulating carcinogen metabolism. *J. Nutr.* 131: 3027S-3033S.
14 Brooks, J. D., Paton, V. G. & Vidanes, G. (2001) Potent induction of phase 2 enzymes in human prostate cells by sulforaphane. *Cancer Epidemiol. Biomark. Prev.* 10: 949-954.
15 McWalter G K, Higgins L G, McLellan L I, Henderson C J, Song L, Thornalley P J, Itoh K, Yamamoto M, Hayes J D. (2004) Transcription factor Nrf2 is essential for induction of NAD(P)H:quinone oxidoreductase 1, glutathione S-transferases, and glutamate cysteine ligase by broccoli seeds and isothiocyanates. *J Nutr* December; 134(12 Suppl):3499S-3506S.
16 Xu C, Shen G, Chen C, Gelinas C, Kong A N. (2005) Suppression of NF-kappaB and NF-kappaB-regulated gene expression by sulforaphane and PEITC through IkappaBalpha, IKK pathway in human prostate cancer PC-3 cells. *Oncogene*. June 30; 24(28):4486-95.
17 Heiss E, Herhaus C, Klimo K, Bartsch H, Gerhauser C. (2001) Nuclear factor kappa B is a molecular target for sulforaphane-mediated anti-inflammatory mechanisms. *J Biol Chem*. 2001 Aug. 24; 276(34):32008-15.
18 Anwar F., Latif S., Ashraf M., Gilani A. H. (2007) *Moringa oleifera*: A food plant with multiple Medicinal Uses. *Phytother Res* 21 17-25.
19 Guevara A. P., Vargas C., Sakurai H., Fujiwara Y., Hashimoto K., Maoka T., Kozuka M., Ito Y., Tokuda H., Nishino H. (1999) An antitumor promoter from *Moringa oleifera* Lam. *Mutation Research* 440: 181-188.
20 yle R A, Raikumar S V (2004). Plasma cell disorder. In Goldman L., Ausiello D A., eds. Cecile textbooks of medicine. 22nd ed. Philadelphia: W.B. Saunders:1184-95.
21 Longo P L (2001). Plasma cell disorders. In Braunwald E, Kasper D, Faucci A. eds Harrison's principles of internal medicine, 15th edn, vol. 1: 727-33.
22 yle R A, Raikumar S V (2004). Multiple Myeloma. *N Engl J Med*, 351: 1860-73.
23 Sirohi B., Powles R. (2004) Multiple Myeloma. *The Lancet*, vol 363: 875-887.
24 Barillari J, Gueyrard D, Rollin P, Iori R. (2001) Barbarea verna as a source of 2-phenylethyl glucosinolate, precursor of cancer chemopreventive phenylethyl isothiocyanate. *Fitoterapia* 72, 760-764.
25 Barillari J, Canistro D, Paolini M, Ferroni F, Pedulli G F, Iori R, Valgimigli L. (2005) Direct antioxidant activity of purified glucoerucin, the dietary secondary metabolite contained in rocket (Eruca sativa Mill.) seeds and sprouts. *J. Agric. Food Chem.* 53, 2475-2482.
26 EEC Regulation No 1864/90 (1990) Enclosure VIII. *Offic. Eur. Commun*. L170: 27-34
27 Pessina A, Thomas R M, Palmieri S, Luisi P L. (1990) An improved method for the purification of myrosinase and its physicochemical characterization. *Arch. Biochem. Biophys*. 280; 383-389.

The invention claimed is:
1. A method for treating multiple myeloma comprising administering an effective amount of a medicament comprising isolated glucomoringin and/or isolated glucomoringin des-thio-glucoside having the following formulas:

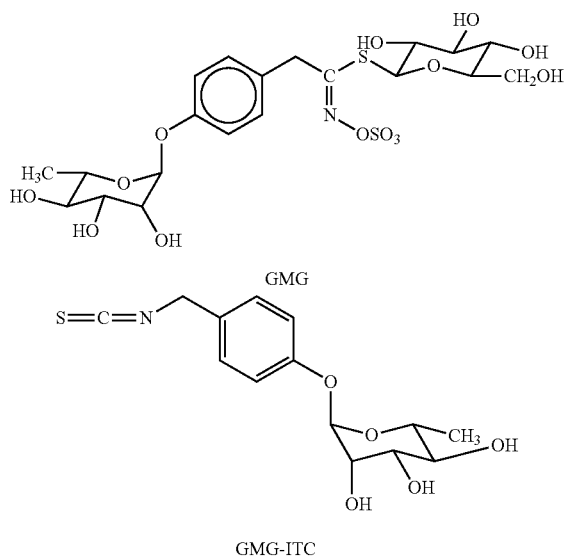

to a patient in need thereof.
2. The method of claim 1, wherein said effective amount ranges from between 1 mg/Kg/day to 30 mg/Kg/day.
3. The method of claim 1, wherein said medicament is isolated glucomoringin.

4. The method of claim 1, wherein said medicament is isolated glucomoringin des-thio-glucoside.

\* \* \* \* \*